United States Patent
Sapey-Triomphe et al.

(10) Patent No.: US 12,145,902 B2
(45) Date of Patent: Nov. 19, 2024

(54) SOLID PRESENTATION FORM OF AT LEAST ONE PHENOL DERIVATIVE AND PROCESS FOR OBTAINING SAME

(71) Applicant: SPECIALTY OPERATIONS FRANCE, Lyons (FR)

(72) Inventors: Rodolphe Sapey-Triomphe, Sérézin-du-Rhône (FR); Cédric Humblot, Lyons (FR)

(73) Assignee: SPECIALTY OPERATIONS FRANCE, Lyons (FR)

( * ) Notice: Subject to any disclaimer, the term of this patent is extended or adjusted under 35 U.S.C. 154(b) by 920 days.

(21) Appl. No.: 17/266,238

(22) PCT Filed: Aug. 2, 2019

(86) PCT No.: PCT/EP2019/070872
§ 371 (c)(1),
(2) Date: Feb. 5, 2021

(87) PCT Pub. No.: WO2020/030541
PCT Pub. Date: Feb. 13, 2020

(65) Prior Publication Data
US 2021/0292262 A1    Sep. 23, 2021

(30) Foreign Application Priority Data
Aug. 9, 2018   (FR) ........................ 1857419

(51) Int. Cl.
*A61K 8/02*       (2006.01)
*A23L 27/20*      (2016.01)
*A61K 9/20*       (2006.01)
*C07C 41/40*      (2006.01)
*C07C 43/23*      (2006.01)

(52) U.S. Cl.
CPC ............ *C07C 43/23* (2013.01); *A23L 27/204* (2016.08); *A61K 8/0216* (2013.01); *A61K 9/2072* (2013.01); *C07C 41/40* (2013.01); *A23V 2002/00* (2013.01); *C07C 2601/16* (2017.05)

(58) Field of Classification Search
CPC ............................ A61K 8/2016; A61K 8/0216
See application file for complete search history.

(56) References Cited

U.S. PATENT DOCUMENTS

| 5,807,584 A | 9/1998 | Le Thiesse et al. |
| 2006/0135730 A1 | 6/2006 | Le Thiesse |
| 2017/0326760 A1 | 11/2017 | Schmidt |

FOREIGN PATENT DOCUMENTS

| EP | 689772 A1 * | 1/1996 | ............ A23G 3/0231 |
| WO | 2004039758 A1 | 5/2004 | |

\* cited by examiner

*Primary Examiner* — Benjamin J Packard
(74) *Attorney, Agent, or Firm* — Osha Bergman Watanabe & Burton LLP

(57) ABSTRACT

The present invention relates to a novel solid presentation form of a phenol derivative, characterized by a rounded portion and a flat portion. The compositions thus obtained have advantageous properties suitable for the storage, handling and flow of the compounds. The present invention also relates to a process for preparing these solids, and to the use thereof, in particular in the polymer and agri-food industries.

20 Claims, 2 Drawing Sheets

SOLID PRESENTATION FORM OF AT LEAST ONE PHENOL DERIVATIVE AND PROCESS FOR OBTAINING SAME

This application is a U.S. national phase entry under 35 U.S.C. § 371 of International Application No. PCT/EP2019/070872, filed on Aug. 2, 2019, which claims priority to French Application No. 1857419, filed on Aug. 9, 2018. The entire contents of these applications are explicitly incorporated herein by this reference.

TECHNICAL FIELD

The present invention relates to a novel solid presentation form of at least one phenol derivative having at least one rounded part and one flat part. The present invention also describes a process for preparing these solids having at least one rounded part and one flat part. The invention also relates to these solids obtained by this preparation process.

PRIOR ART

Phenol derivatives, such as vanillin, ethylvanillin, hydroquinone, catechol, para-methoxyphenol, are present in many industrial fields. They are, for example, used by the agrifood industry as flavorings, or in the polymer industry as a polymerization inhibitor.

Currently these compounds are mainly sold in powder form. Document WO 2016/033157 describes methods of shaping hydroquinone in the form of crystalline powder. This powder consists of small brittle needles, the result of which is a sizeable presence of fines which poses a problem in particular for the storage, handling and transportation thereof. The caking resistance of this product is certainly slightly improved, but the handling of this compound presents risks in particular of irritation to the eyes, the respiratory system or the skin.

Alternative forms have been proposed. Document JP 2000/302716 describes a granulation technique which consists in passing the powder between two rollers making it possible to obtain slabs and then crushing these slabs so as to obtain granules. The disadvantage of this process is that dust may remain, either because of the passage through the rollers of the compactor, or by the attrition of the slabs in the crusher. In addition, the granules are compact and their dissolution rate is very low compared to the initial powder.

Documents EP 0689772 and WO 2004/039758 describe the shaping of phenolic compounds in the form of beads, in particular hydroquinone and vanillin by prilling methods. These beads are highly spherical. This particular presentation form gives the beads advantageous properties of resistance to attrition, and would thus avoid the formation of a large amount of dust. The prilling methods for preparing these compounds consist in cooling droplets of a phenolic compound in a gas stream in order to solidify them. For some specific applications, the dissolution rate of these beads could be improved.

Moreover, despite the recognized advantages of these alternative methods, these methods are expensive. It is therefore desirable to propose other alternatives whose economic impact is lower while maintaining good storage, handling, transportation, resistance to attrition and resistance to caking properties, while reducing the risks related to health and to the environment by minimizing the presence of dust and fines and improving the solubility properties of these presentation forms.

BRIEF DESCRIPTION

It is to the credit of the Applicant Company to have identified a novel solid presentation form exhibiting all of the abovementioned desired characteristics and in particular good solubility properties while maintaining good resistance to attrition properties.

A first aspect of the present invention relates to a novel solid presentation form comprising at least one compound of formula (I)

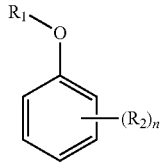

Formula (I)

in which:
  n is between 0 and 5, preferably between 0 and 4, and preferentially n is equal to 0, 1 or 2,
  $R_1$ is selected from the group consisting of hydrogen, alkyl, and alkenyl, preferably $R_1$ is selected from hydrogen, methyl and ethyl,
  $R_2$ is selected from the group consisting of hydroxyl, alkyl, alkenyl, alkynyl, alkoxy, formyl and acyl, preferably $R_2$ is selected from hydroxyl, methyl, ethyl, propyl, methoxy, ethoxy and formyl,
and comprising at least one rounded part and one flat part.

According to another aspect, the present invention relates to a process for preparing a novel solid presentation form comprising at least one compound of formula (I) comprising at least the following steps:
  (a) a step wherein liquid droplets comprising at least one compound of formula (I) are arranged on a flat surface,
  (b) a step of solidifying said droplets on said surface.

Finally, the present invention relates to the novel solids capable of being obtained by the process of the present invention. Finally, the present invention relates to the use of these novel solids in industry.

DETAILED DESCRIPTION

Figure 1:
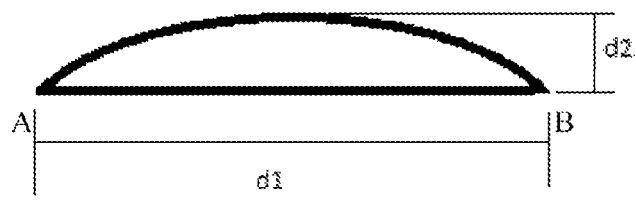
FIGS. 1 and 2 show two cross-sectional views of an embodiment of a solid compound according to the invention.

In the context of the present invention, and unless otherwise indicated, the expression "between . . . and . . . " includes the limits.

In the context of the present invention, and unless otherwise indicated, the expression "alkyl" represents a linear or branched saturated hydrocarbon chain comprising from 1 to 6 carbon atoms.

In the context of the present invention, and unless otherwise indicated, the expression "alkoxy" represents OR where R is an alkyl group as defined above.

In the context of the present invention, and unless otherwise indicated, the expression "alkenyl" represents a linear or branched unsaturated hydrocarbon chain comprising from 1 to 6 carbon atoms and bearing at least one double bond between two carbon atoms.

In the context of the present invention, and unless otherwise indicated, the expression "alkynyl" represents a linear or branched unsaturated hydrocarbon chain comprising from 1 to 6 carbon atoms and bearing at least one triple bond between two carbon atoms.

In the context of the present invention, the term "comprising" may have the meaning of "consisting of".

In the context of the present invention, the term "ambient temperature" means a temperature between 19° C. and 24° C., preferably the ambient temperature is equal to 20° C.

According to a first aspect, the present invention relates to a novel solid presentation form comprising at least one compound of formula (I)

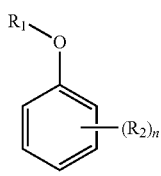

Formula (I)

wherein:
n is between 0 and 5, preferably between 0 and 4, and preferentially n is equal to 0, 1 or 2,
$R_1$ is selected from the group consisting of hydrogen, alkyl and alkenyl,
$R_2$ is selected from the group consisting of hydroxyl, alkyl, alkenyl, alkynyl, alkoxy, formyl and acyl,
and comprising at least one rounded part and one flat part.

According to a preferred aspect, $R_1$ is selected from hydrogen, methyl and ethyl. According to another preferred aspect, $R_2$ is selected from hydroxyl, methyl, ethyl, propyl, methoxy, ethoxy and formyl.

According to a preferred aspect of the present invention in which n=2, the $R_2$ groups, which are identical or different, are placed relative to the ORI group, one in the ortho position and the other in the para position.

According to another aspect of the present invention in which n=1, the $R_2$ group is placed in the ortho or para position relative to the ORI group.

According to a preferred aspect, the compounds of formula (I) are selected from the group consisting of hydroquinone, catechol, resorcinol, pyrogallol, 4-tert-butylcatechol, tert-butylhydroquinone, para-methoxyphenol, butylhydroxyanisole, vanillin, ethylvanillin and a compound of vanillin and ethylvanillin in a molar ratio of 2. Preferably, the compounds of formula (I) are selected from the group consisting of hydroquinone, catechol, resorcinol, pyrogallol, 4-tert-butylcatechol, tert-butylhydroquinone, para-methoxyphenol and butylhydroxyanisole. Alternatively, the compounds of formula (I) are chosen from the group consisting of vanillin, ethylvanillin and a compound of vanillin and ethylvanillin in a molar ratio of 2.

According to a preferred embodiment, the compound of formula (I) is a polymerization inhibitor.

According to another preferred embodiment, the compound of formula (I) is a flavoring.

According to one aspect of the present invention, the novel solid presentation form may comprise one, two or three compounds of formula (I) as defined above, preferably the novel solid presentation form according to the present invention comprises a compound of formula (I) or a mixture of two compounds of formula (I).

In the case where the novel solid presentation form according to the invention comprises 2 compounds of formula (I), the molar ratio between the 2 compounds is between 1:99 and 99:1. According to one particular aspect, the molar ratio between the two compounds is 1:1 or 2:1.

In the case where the novel solid presentation form according to the invention comprises 2 compounds of formula (I), the mass ratio is strictly greater than 0% by weight, preferably greater than or equal to 0.1% by weight, more preferentially greater than or equal to 5% by weight and strictly less than 100% by weight.

According to a particular aspect, the novel solid presentation form according to the present invention may comprise at least one additive selected from the group consisting of antioxidants, antifoams, corrosion inhibitors, rust inhibitors, surfactants, detergents, dispersants, antifouling agents, thinners, viscosifiers, or acidity correctors.

According to a particular aspect, the novel solid presentation form according to the present invention may comprise at least one compound selected from the group consisting of tocopherol derivatives, preferably α-tocopherol, β-tocopherol, γ-tocopherol, δ-tocopherol, copper complexes having an oxidation state of 2, preferably copper acetate $(Cu(OAc)_2)$ or copper dibutyldithiocarbamate (CB), 2-sec-butyl-4,6-dinitrophenol, phenylenediamine, TEMPO, TEMPO-OH, 2,4-dimethyl-6-tertbutylphenol (Topanol A), phenothiazine, butylhydroxyanisole (BHA) and 2,6-di-tert-butyl-4-methoxyphenol (DTBHA).

Advantageously, the novel solid presentation form according to the present invention comprises:
between 50% and 100% by weight of at least one compound of formula (I) as defined above, and
between 0% and 50% by weight of at least one compound selected from the group consisting of tocopherol derivatives, preferably α-tocopherol, β-tocopherol, γ-tocopherol, δ-tocopherol, copper complexes having an oxidation state of 2, preferably copper acetate (Cu$(OAc)_2$) or copper dibutyldithiocarbamate (CB), 2-sec-butyl-4,6-dinitrophenol, phenylenediamine, TEMPO, TEMPO-OH, 2,4-dimethyl-6-tertbutylphenol (Topanol A), phenothiazine, butylhydroxyanisole (BHA) and 2,6-di-tert-butyl-4-methoxyphenol (DTBHA).

According to another particular aspect, the novel solid presentation form according to the present invention may comprise at least one additive selected from the group consisting of fatty substances, waxes, sugars, polysaccharides such as starches, maltodextrins and antioxidants.

Figure 2:
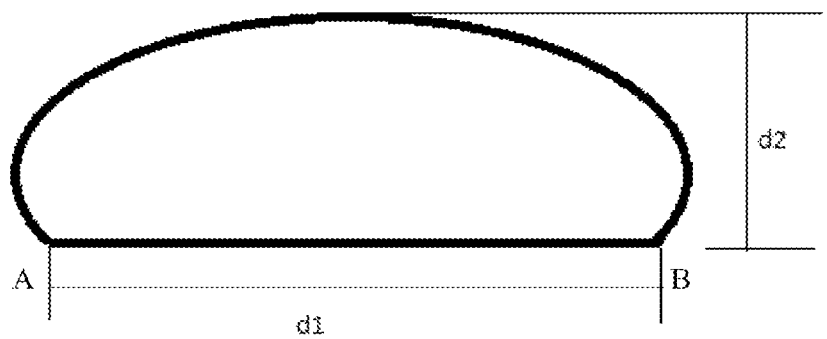

The novel solid presentation form according to the present invention may be represented schematically as indicated in FIGS. 1 and 2. The distance d1 represents the greatest distance between the 2 points A and B of the flat part of the novel solid presentation form. The distance d2 represents the greatest distance between the flat part and the rounded part. The novel solid presentation forms of the present invention can be likened to spherical caps.

The rounded part of these novel solid presentation forms is preferably spherical, however it may have imperfections. The novel solid presentation forms according to the present invention may be described as pellets.

According to the present invention, the novel solid form has at least one rounded part and one flat part. Thus according to the present invention, the novel solid form has an edge.

Figure 3:
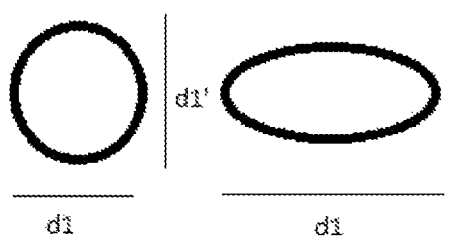
FIG. 3 shows a top or bottom view of a solid compound according to the invention.

According to a particular aspect of the present invention, the flat part, top or bottom view as shown schematically in FIG. 3, of the novel solid presentation form may have a shape similar to a disk or an ellipse.

The volume of the spherical cap may be calculated according to the following formula:

$$V = \frac{\pi d_2^2 (3^{d_1/2} - d_2)}{3}$$

wherein d1 is the diameter of the spherical cap (see FIG. 3) and d2 is the thickness of the spherical cap.

The novel solid form according to the present invention may therefore be likened to a portion of a sphere of radius r ($V=4\pi r^3/3$) or a portion of an ellipsoid ($V=4\pi abc/3$, where a, b and c are the lengths of the semi-axes of the ellipsoid). The volume of this portion may therefore be measured according to the following formulae:

$$V = \frac{4\pi r^3}{3} x \text{ or } V = \frac{4\pi abc}{3} x$$

wherein x is strictly greater than 0, preferably greater than or equal to 0.01, and more preferentially greater than or equal to 0.02, x is strictly less than 1, preferably less than or equal to 0.9, more preferentially less than or equal to 0.8. According to one particular aspect, x may be between 0.01 and 0.1.

According to a particular aspect of the present invention, d1 and d1', which are identical or different, are between 300 µm and 10 000 µm, preferably between 500 µm and 5000 µm, more preferentially between 500 and 2000 µm; d2 is between 50 µm and 10 000 µm, preferably between 75 µm and 5000 µm and more preferentially between 75 µm and 2000 µm.

According to the present invention, the flat part of the novel solid forms is a continuous surface. Preferably, the flat surface represents at least 5%, preferably at least 10%, 15%, 20%, 25%, 30%, 40%, 50% of the total surface of the novel solid form according to the present invention. Preferably the flat surface represents at most 95%, preferably at most 90%, 85%, 80%, 75%, 70%, 60%, 55% of the total surface of the novel solid form according to the present invention.

The present invention also relates to a process for preparing the novel solid presentation forms as defined above by a pelletizing process. Documents US 2017/0326760 and EP1042056 present two devices suitable for the preparation of pellets according to the invention.

According to one particular aspect, the process comprises at least the following steps:
  (a) a step wherein liquid droplets comprising at least one compound of formula (I) are arranged on a flat surface,
  (b) a step of solidifying said droplets on said surface.

Step (a) is a step of arranging the droplets on a flat surface. In the context of the present invention, the flat surface may be a belt, a plate or a disk. Preferably the belt or disk is in motion.

The belt may be a conveyor belt which rotates around two rolls. The belt performs a translational movement. The droplets are arranged on the upper part of the conveyor belt.

Alternatively, the disk may be rotated around an axis. Preferably, the axis of rotation is perpendicular to the ground. The droplets are arranged on the surface of the disk, preferably the upper surface.

Advantageously, the process of the present invention further comprises a step (a1), before step (a), wherein the at least one compound of formula (I) is melted. During step (a1), the at least one compound of formula (I) is heated to a temperature between 1° C. and 50° C. above its melting point or, in the case of a mixture, the melting point of the compound having the highest melting point, preferably between 1° C. and 20° C. above its melting point, or the melting point of the compound having the highest melting point, and more preferentially preferably between 1° C. and 10° C. above its melting point, or the melting point of the compound having the highest melting point. Generally, the heating temperature may be between 50° C. and 300° C., preferably between 50° C. and 260° C.

An additive or several additives as defined above may be added to the preparation of the compound in molten form.

The method of the present invention may also comprise a step (a2) consisting in forming droplets. The droplet-forming device may be a perforated cylinder or a perforated plate. The droplet-forming device is preferably maintained at a temperature above or equal to the temperature of step (a1). Preferably, the droplet-forming device is located above the flat surface so that the droplets may fall onto the flat surface.

According to one particular aspect, step (a1) is carried out before step (a2). According to another aspect, the droplet-forming step (a2) is carried out directly at the end of a process for preparing or purifying a compound of formula (I). In this embodiment, the compound of formula (I) is in liquid form without requiring a step in which the compound of formula (I) is melted.

Step (b) is a step of solidifying the droplets on the flat surface. Advantageously, the flat surface is cooled to a temperature strictly below the melting point of the compound of formula (I) or, in the case of a mixture, strictly below the melting point of the compound of formula (I) having the lowest melting point. Advantageously, the flat surface is cooled to a temperature between -50° C. and a temperature strictly below the melting point of the compound of formula (I) or, in the case of a mixture, strictly below the melting point of the compound of formula (I) having the lowest melting point, preferably to a temperature between 0° C. and a temperature strictly below the melting point of the compound of formula (I) or, in the case of a mixture, strictly below the melting point of the compound of formula (I) having the lowest melting point, and more preferentially to a temperature between 10° C. and a temperature strictly below the melting point of the compound of formula (I) or, in the case of a mixture, strictly below the melting point of the compound of formula (I) having the lowest melting point. Preferably the flat surface is cooled to a cooling temperature between 10° C. and ambient temperature.

According to a particular aspect of the present invention, the cooling temperature of the flat surface is uniform over the entire flat surface. According to another particular aspect, the cooling temperature is not uniform over the entire flat surface, the temperature may have a cooling gradient or cooling zones in which the flat surface is cooled to different cooling temperatures.

According to one particular aspect, the flat surface may have undergone a surface treatment prior to the process according to the present invention. The flat surface may also be coated in particular with a nonstick or hydrophobic coating, such as PTFE (polytetrafluoroethylene). The flat surface may also have roughnesses. These treatments or roughnesses make it possible in particular to improve the detachment of the novel solid forms according to the present invention at the end of the process. These treatments or roughnesses also make it possible to improve the mechanical properties of the novel solid forms according to the present invention, in particular better resistance to friability during handling operations. The shape of the solids according to the present invention also makes it possible to reduce caking phenomena.

At the end of the solidification step (b), the novel solid presentation forms according to the present invention may adhere to the flat surface. The process according to the present invention may comprise a step in which the novel solid presentation forms are removed from the flat surface. The device for forming the novel solid presentation forms according to the present invention may comprise a knife or scraper.

According to a particular aspect of the present invention, the process may be carried out in air, under oxygen, or under a controlled atmosphere, in particular the degree of humidity may be controlled. The process according to the invention may be carried out under dry air, under an inert atmosphere, in particular under nitrogen.

At the end of the process according to the present invention, the content of fine particles having a size less than or equal to 355 µm is less than or equal to 30%, preferably less than or equal to 20%, more preferentially less than or equal to 10%, and even more preferentially less than or equal to 0.1% by weight relative to the weight of novel solid presentation form of formula (I).

The process according to the present invention may also comprise a step in which the fine particles, having a size less than or equal to 355 µm, are separated by screening or by cycloning. The fine particles may be recycled.

The novel solid compounds according to the present invention have a hardness of at least 1 N. The hardness may be measured with a penetrometer.

Advantageously, the novel solid compounds according to the present invention have a friability of less than or equal to 15%. This parameter allows easier handling of these novel solid compounds compared to powder, because the formation of mist is avoided or at least reduced. The friability may be measured by mixing the novel solid presentation forms according to the present invention in a triaxial mixer for 10 minutes, then by measuring the content of particles smaller than 100 µm produced. The friability represents the ratio between the mass of particles smaller than 100 µm produced and the total mass of the novel solid presentation forms introduced into the triaxial mixer.

The novel solid presentation forms according to the present invention have good dissolution properties. The rate of dissolution of these solids is at least equivalent to, preferably better than, the rate of dissolution of other existing forms of compounds of formula (I).

The chemical composition of the novel solid presentation forms according to the present invention depends on the liquid composition as defined above.

The addition of additives as defined above in the novel solid presentation forms according to the present invention may be carried out during the preparation of the composition comprising at least one compound of formula (I) in liquid form (Step (a1)) or during an additional step at the end of the process.

The novel solid presentation forms comprising at least one compound of formula (I) as defined above which can be obtained according to the process of the invention are also one subject of the present invention.

Finally, the present invention relates to the use of these novel solid presentation forms comprising at least one compound of formula (I) in industry, in particular the polymer, agri-food, perfume or pharmaceutical industry.

EXAMPLE

Pellets of para-methoxyphenol (PMP) are prepared. The PMP is first melted at 80° C. Droplets are then formed and deposited on a belt cooled to 18° C.

Figure 4:
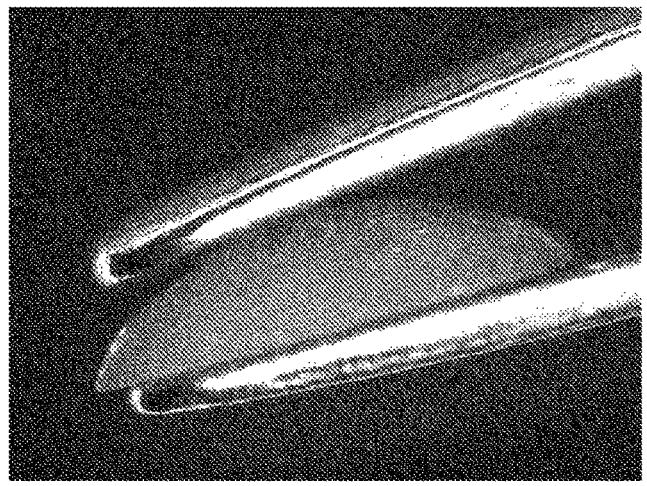
FIG. 4 is a photo of a pellet of para-methoxyphenol according to the present invention obtained on a stainless steel surface (optical microscope, 6.3× magnification).
Figure 5:
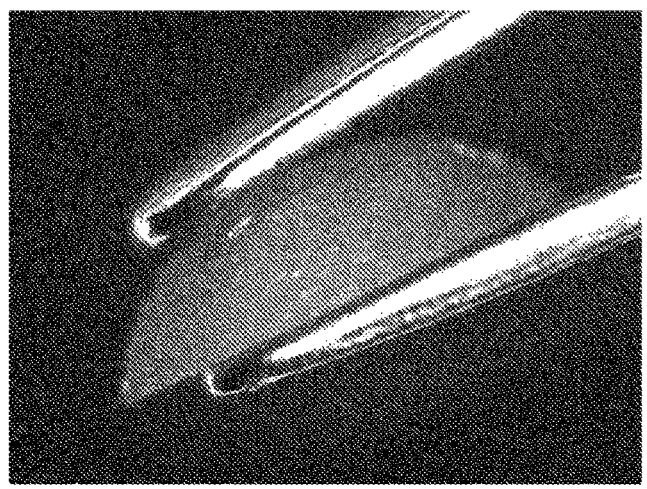
FIG. 5 is a photo of a pellet of para-methoxyphenol according to the present invention obtained on a PTFE-coated surface (optical microscope, 6.3× magnification).

FIGS. 4 and 5 show pellets according to the present invention.

Example 1: The pellets of FIG. 4 were obtained on a stainless steel belt.

Example 2: The pellets of FIG. 5 were obtained on a PTFE-coated belt.

|  | Pellets of Ex. 1 | Pellets of Ex. 2 | PMP powder | PMP flakes |
|---|---|---|---|---|
| Diameter (µm) | 7140 | 5500 | N/A | Length: 0.5 to 4 cm |
| Thickness (µm) | 921 | 1230 | N/A | 1000 to 2000 |
| Resistance to caking | ++ | ++ | -- | - |
| Dissolution rate in acrylic acid | + | + | +++ | ++ |
| Dissolution rate in water | + | + | +++ | ++ |

The resistance to caking is acquired visually after storage of the sample for 7 days at 35° C.

The dissolution rate corresponds to the time required to dissolve 90% of 2 g of pellets/powder/flakes in 100 g of water/acrylic acid at 20° C. stirred at 300 rpm.

The invention claimed is:

1. A novel solid presentation form comprising at least one rounded part; a pellet; or a spherical cap; wherein the novel solid presentation form, pellet, or spherical cap comprises at least one compound of formula (I)

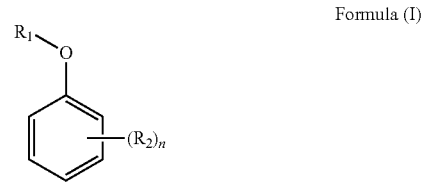

Formula (I)

wherein:
n is between 0 and 5,
$R_1$ is selected from the group consisting of hydrogen, alkyl, and alkenyl,
$R_2$ is selected from the group consisting of hydroxyl, alkyl, alkenyl, alkynyl, alkoxy, formyl, and acetyl, and
the novel presentation form, the pellet, and the spherical cap each comprise at least one flat part that is a continuous surface and represents at least 5% of the total surface of each of the novel presentation form, the pellet and the spherical cap.

2. The novel presentation form, pellet, or spherical cap as claimed in claim 1, wherein the compound of formula (I) is selected from the group consisting of hydroquinone, catechol, resorcinol, pyrogallol, 4-tert-butylcatechol, tert-butylhydroquinone, para-methoxyphenol, butylhydroxyanisole, vanillin, ethylvanillin and a compound of vanillin and ethylvanillin in a molar ratio of 2.

3. A process for preparing a novel solid presentation form, a pellet or a spherical cap comprising at least one compound of formula (I) as defined in claim 1, the process comprising at least the following consecutive steps:
(a) arranging liquid droplets comprising at least one compound of formula (I) on a flat surface,
(b) a step of solidifying said droplets on said surface.

4. The process as claimed in claim 3, wherein the flat surface is a band, a plate, or a disk.

5. The process as claimed in claim 3, further comprising step (a1) heating the at least one compound of formula (I) to a temperature between 1° C. and 50° C. above its melting point before step (a).

6. The process as claimed in claim 3, further comprising a step (a2) forming droplets before step (a).

7. The process as claimed in claim 3, wherein the flat surface is cooled to a temperature strictly below the melting point of the compound of formula (I) to allow the solidification of said droplets.

8. The process as claimed in claim 3, wherein the process is carried out in air, under oxygen, oxygen-depleted air, controlled atmosphere, or inert atmosphere.

9. A novel solid presentation form comprising at least one rounded part and one flat part, pellet, or spherical cap comprising at least one compound of formula (I)

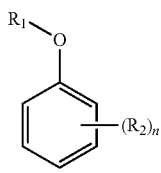

Formula (I)

in which:
n is between 0 and 5,
$R_1$ is selected from the group consisting of hydrogen, alkyl, and alkenyl,
$R_2$ is selected from the group consisting of hydroxyl, alkyl, alkenyl, alkynyl, alkoxy, formyl, and acetyl,
which can be obtained according to the process defined in claim 3.

10. The novel solid presentation form comprising at least one rounded part and one flat part; the pellet; or the spherical cap of claim 1, wherein n is between 0 and 4.

11. The novel solid presentation form comprising at least one rounded part and one flat part; the pellet; or the spherical cap of claim 10, wherein n is equal to 0, 1 or 2.

12. The novel solid presentation form comprising at least one rounded part and one flat part; the pellet; or the spherical cap of claim 1, wherein $R_1$ is selected from hydrogen, methyl and ethyl.

13. The novel solid presentation form comprising at least one rounded part and one flat part; the pellet; or the spherical cap of claim 1, wherein $R_2$ is selected from hydroxyl, methyl, ethyl, propyl, methoxy, ethoxy and formyl.

14. The process as claimed in claim 5, wherein the at least one compound of formula (I) is heated to a temperature between 1° C. and 20° C. above its melting point.

15. The process as claimed in claim 14, wherein the at least one compound of formula (I) is heated to a temperature between 1° C. and 10° C. above its melting point.

16. The process as claimed in claim 8, wherein the inert atmosphere Is under nitrogen.

17. A composition comprising the novel solid presentation form, pellet, or spherical cap as defined in claim 1.

18. The composition of claim 17, wherein the composition is a polymer, agri food, perfume, or pharmaceutical composition.

19. The novel solid presentation form comprising at least one rounded part; a pellet; or a spherical cap of claim 1, wherein the novel solid presentation form, pellet, or spherical cap comprises:
between 50% and 100% by weight of at least one compound of formula (I); and
between 0% and 50% by weight of at least one compound selected from the group consisting of tocopherol derivatives.

20. The novel solid presentation form comprising at least one rounded part; a pellet; or a spherical cap of claim 19, wherein the tocopherol derivatives comprise one or more selected from α-tocopherol, β-tocopherol, γ-tocopherol, δ-tocopherol, copper complexes having an oxidation state of 2, preferably copper acetate (Cu(OAc)$_2$) or copper dibutyldithiocarbamate (CB), 2-sec-butyl-4,6-dinitrophenol, phenylenediamine, TEMPO, TEMPO-OH, 2,4-dimethyl-6-tert-butylphenol (Topanol A), phenothiazine, butylhydroxyanisole (BHA) and 2,6-di-tert-butyl-4-methoxyphenol (DTBHA).

* * * * *